US008658777B2

(12) United States Patent
Umezawa et al.

(10) Patent No.: US 8,658,777 B2
(45) Date of Patent: Feb. 25, 2014

(54) ACTIVATED PROTEASE INDICATOR

(75) Inventors: Yoshio Umezawa, Tokyo (JP); Takeaki Ozawa, Aichi (JP); Akira Kanno, Tokyo (JP)

(73) Assignees: The University of Tokyo, Tokyo (JP); Inter-University Research Institute Corporation National Institutes of Natural Sciences, Tokyo (JP)

( * ) Notice: Subject to any disclaimer, the term of this patent is extended or adjusted under 35 U.S.C. 154(b) by 663 days.

(21) Appl. No.: 12/451,341

(22) PCT Filed: May 9, 2008

(86) PCT No.: PCT/JP2008/058669
§ 371 (c)(1),
(2), (4) Date: Feb. 19, 2010

(87) PCT Pub. No.: WO2008/140060
PCT Pub. Date: Nov. 20, 2008

(65) Prior Publication Data
US 2010/0297620 A1 Nov. 25, 2010

(30) Foreign Application Priority Data
May 9, 2007 (JP) .................................. 2007-124924

(51) Int. Cl.
*C07K 1/00* (2006.01)
(52) U.S. Cl.
USPC ........................................................ 536/23.4
(58) Field of Classification Search
None
See application file for complete search history.

(56) References Cited

U.S. PATENT DOCUMENTS

2005/0153310 A1* 7/2005 Fan et al. ........................... 435/6

FOREIGN PATENT DOCUMENTS

| EP | 1 229 330 | 8/2002 |
|----|-----------|--------|
| EP | 1 541 679 | 6/2005 |
| EP | 1 634 960 | 3/2006 |
| EP | 1 731 603 | 12/2006 |

OTHER PUBLICATIONS

Naqvi et al, Beta galactosidase enzyme fragment complementation as a high-throughput screening protease technology. J Biomol Screen. Aug. 2004;9(5):398-408.*
Evans et al, Protein trans-splicing and cyclization by a naturally split intein from the dnaE gene of *Synechocystis* species PCC6803. J Biol Chem. Mar. 31, 2000;275(13):9091-4.*
International Search Report issued Jul. 29, 2008 in International (PCT) Application No. PCT/JP2008/058669.
Nijhawan D et al. Apoptosis in neural development and disease. Annu Rev Neurosci. 2000;23:73-87.
Rideout HJ et al. Caspase inhibition: a potential therapeutic strategy in neurological diseases. Histol Histopathol. Jul. 2001;16(3):895-908.
Neefjes J et al. Fluorescent probes for proteolysis: tools for drug discovery. Nat Rev Drug Discov. Jan. 2004;3(1):58-69.
Reits E et al. Peptide diffusion, protection, and degradation in nuclear and cytoplasmic compartments before antigen presentation by MHC class I. Immunity. Jan. 2003;18(1):97-108.
Nagai T et al. A high-throughput method for development of FRET-based indicators for proteolysis. Biochem Biophys Res Commun. Jun. 18, 2004;319(1):72-7.
Takemoto K et al. Spatio-temporal activation of caspase revealed by indicator that is insensitive to environmental effects. J Cell Biol. Jan. 20, 2003 ;160(2):235-43.
Xu X et al. Detection of programmed cell death using fluorescence energy transfer. Nucleic Acids Res. Apr. 15, 1998;26(8):2034-5.
Mahajan NP et al. Novel mutant green fluorescent protein protease substrates reveal the activation of specific caspases during apoptosis. Chem Biol. Jun. 1999;6(6):401-9.
Weissleder R et al. Shedding light onto live molecular targets. Nat Med. Jan. 2003;9(1):123-8.
Laxman B et al. Noninvasive real-time imaging of apoptosis. Proc Natl Acad Sci U S A. Dec. 24, 2002;99(26):16551-5.
Kim SB et al. High-throughput sensing and noninvasive imaging of protein nuclear transport by using reconstitution of split *Renilla* luciferase. Proc Natl Acad Sci U S A. Aug. 10, 2004;101(32):11542-7.
Rogers S et al. Amino acid sequences common to rapidly degraded proteins: the PEST hypothesis. Science. Oct. 17, 1986;234(4774):364-8.
Rechsteiner M et al. PEST sequences and regulation by proteolysis. Trends Biochem Sci. Jul. 1996;21(7):267-71.
Guzikowski AP et al. Cyclic peptidase substrates for fluorescent analysis of Caspase 3 enzyme activity. Proc SPIE. 2000;3913:54-63.
Kanno A et al. Cyclic luciferase for real-time sensing of caspase-3 activities in living mammals. Angew Chem Int Ed Engl. 2007;46(40):7595-9.

(Continued)

*Primary Examiner* — Sheridan Swope
(74) *Attorney, Agent, or Firm* — Wenderoth, Lind & Ponack, L.L.P.

(57) ABSTRACT

It is an object of the invention to provide novel approaches capable of detecting activated protease and also detecting protease activation on real time at a high sensitivity in a noninvasive manner. By the method for detecting activated protease of the invention, an indicator in a circular form comprising the C-half fragment of luciferase (Luc-C) and the N-half fragment of luciferase (Luc-N) linked together through a substrate peptide for a protease is introduced in an in vitro assay system or in cells. Upon digestion of the substrate peptide by the protease, Luc-N and Luc-C together reconstructs active luciferase, so that the activated protease can be detected by assaying the luminescence signal from the luciferase.

7 Claims, 8 Drawing Sheets

(56) References Cited

OTHER PUBLICATIONS

Ghoda L et al. Prevention of rapid intracellular degradation of ODC by a carboxyl-terminal truncation. Science. Mar. 17, 1989;243(4897):1493-5.

Kim SB et al. Integrated molecule-format bioluminescent probe for visualizing androgenicity of ligands based on the intramolecular association of androgen receptor with its recognition peptide. Anal Chem. Mar. 1, 2007;79(5):1874-80.

* cited by examiner

SEQUENCE LISTING

```
<160> NUMBER OF SEQ ID NOS: 4

<210> SEQ ID NO 1
<211> LENGTH: 4
<212> TYPE: PRT
<213> ORGANISM: Artificial sequence
<220> FEATURE:
<223> OTHER INFORMATION: Synthetic construct

<400> SEQUENCE: 1

Asp Glu Val Asp
1

<210> SEQ ID NO 2
<211> LENGTH: 4
<212> TYPE: PRT
<213> ORGANISM: Artificial sequence
<220> FEATURE:
<223> OTHER INFORMATION: Synthetic construct

<400> SEQUENCE: 2

Leu Glu Thr Asp
1

<210> SEQ ID NO 3
<211> LENGTH: 4
<212> TYPE: PRT
<213> ORGANISM: Artificial sequence
<220> FEATURE:
<223> OTHER INFORMATION: Synthetic construct

<400> SEQUENCE: 3

Leu Glu His Asp
1

<210> SEQ ID NO 4
<211> LENGTH: 4
<212> TYPE: PRT
<213> ORGANISM: Artificial sequence
<220> FEATURE:
<223> OTHER INFORMATION: Synthetic construct

<400> SEQUENCE: 4

Leu Leu Val Tyr
1
```

ACTIVATED PROTEASE INDICATOR

This application is a U.S. national stage of International Application No. PCT/JP2008/058669 filed May 9, 2008.

TECHNICAL FIELD

The present invention relates to an activated protease indicator, and an indicator of protease activation capable of noninvasive real-time detection of protease activation at a high sensitivity.

BACKGROUND ART

Eukaryotic cells contain many proteases involved in cell growth, division, differentiation, migration, and intra- or extracellular signaling. One of the complicated proteolytic signaling processes is used to decide programmed cell death or apoptosis. Improper apoptosis causes many diseases including Alzheimer disease, Huntington disease, ischemia, autoimmune disorder and immortality of cancer cells [Nijhawan, D. et al. (2000) Annu. Rev. Neurosci. 23, 73-87; Rideout, H. J. & Stefanis, L. (2001) Histol. Histopathol. 16, 895-908]. For example, as cytosolic caspases play a central role in mediating the initiation and propagation of apoptosis, chemical compounds that can either inhibit or accelerate caspase activity are a major concern. Also, an understanding of the physiological proteolytic processes inside living organisms is of crucial importance for assessing the roles of proteases in normal states and diseases. Hence, the development of a rapid screening system to detect a protease activity and a noninvasive method to image apoptosis is essential for the discovery of novel compounds that are potential therapeutic chemicals [Neefjes, J. & Dantuma, N. P. (2004) Nat. Rev. Drug Discov. 3, 58-69]. These developments would provide new insights into the mechanism of apoptosis.

Several methods for monitoring protease activities have been developed; the use of peptide substrates containing a fluorescence resonance energy transfer (FRET) pair, such as fluorescein and tetramethylrhodamine, is a simple strategy for the detection of proteolytic activities [Reits, E. et al, (2003) Immunity, 18, 97-108]. D-Luciferin connected with a peptide substrate for a caspase enables highly sensitive detection of a caspase activity in vitro. However, these chemical probes do not diffuse across membranes. These methods therefore require complex assay procedures like preparation of cell lysates and elimination of sediments upon analysis of intracellular protease.

Genetically encoded fluorescent indicators that include green fluorescent protein (GFP) derivatives overcome this drawback. A potential advantage of the indicator is no need of introducing any peptide substrate into living cells [Nagai, T. & Miyawaki, A. (2004) Biochem. Biophys. Res. Commun. 319, 72-7; Takemoto, K. et al. (2003) J. Cell. Biol. 160, 235-43; Xu, X. et al. (1998) Nucleic Acids Res. 26, 2034-5; Mahajan, N. P. et al. (1999) Chem. Biol. 6, 401-9]. These indicators became valuable tools for studying temporal caspase activities in single living cells. However, the results obtained are not quantitative but rather qualitative, since the changes in the fluorescence signals are very small and the number of cells that can be analyzed is limited. In addition, it is difficult to apply the indicators to living animals because the light for excitation of the fluorophores is mostly absorbed by their tissues [Weissleder, R. & Ntziachristos, V. (2003) Nat. Med. 9, 123-8].

A recombinant bioluminescent indicator for monitoring caspase activities has been developed by using *Photinus pyralis* luciferase (firefly luciferase, Fluc) [Laxman B. et al. (2002) Proc. Natl. Acad. Sci. USA. 99, 16551-5]. The indicator is composed of Fluc sandwiched between estrogen-receptor regulatory domains with an Asp-Glu-Val-Asp (DEVD) sequence that can be digested by caspase-3. The usefulness of the bioluminescent indicator has been validated. That is, the activity of caspase-3 was monitored noninvasively over time in living animals. However, the molecular size of the indicator is quite large and the intensity of the luminescence signals is relatively low because of insufficient digestion of the DEVD sequence during apoptosis.

The inventors made inventions of probes binding to various target molecules in living cells as well as indicators for detecting the activities of the target molecules, utilizing the reconstruction of reporter molecules through a protein splicing with intein, and filed patent applications thereof (for example, JP-A-2004-108943; JP-A-2004-104222; JP-A-20002-088766; WO 2005/085439).

DISCLOSURE OF THE INVENTION

Problems that the Invention is to Solve

As described above, it is sufficiently understood the importance of detecting protease activation in living cells (especially, cells in animals). By, however, the prior techniques could not achieve a noninvasive real-time detection of protease activities in living cells (especially, living cells in animals) at a high sensitivity.

An object of the invention is to provide novel approaches capable of detecting activated protease and also detecting protease activation on real time at a high sensitivity in a noninvasive manner.

Means for Solving the Problems

The invention provides an activated protease indicator, which is a circular form comprising a C-half fragment of luciferase (Luc-C) and a N-half fragment of luciferase (Luc-N) linked together through a substrate peptide for a protease, and the Luc-N and the Luc-C reconstruct an activated luciferase upon digestion of the substrate peptide by the protease.

The indicator of the invention, at the state of circular form, cannot generate any signals because the luciferase is distorted. If the substrate sequence is digested by a protease, the luciferase changes into an active form and restores its activity.

Luc-C and Luc-N are molecules prepared by splitting a single luciferase into two fragments. In this case, the "single luciferase" may include a full-length luciferase or a part of a luciferase required for the luminescent function. Additionally, these "half fragments" are a state that the luciferase is split at a site where the C-terminal amino acid residue of the Luc-N and the N-terminal residue of the Luc-C can be ligated together with a peptide bond so that the resulting product can restore the luminescent function upon the protein splicing with an intein as described below.

In the invention, the "protease" means a sequence-specific protease (for example, caspase) recognizing a specific sequence of a peptide for its digesting, never including proteolytic enzymes (for example, trypsin) that sequentially decompose a peptide from one end thereof or digest a peptide in a sequence-nonspecific manner. The specific sequence to be recognized may be any sequences not existed in luciferase, with no limitation to the length thereof. For the specificity, preferably, the sequence may be four residues or more. The recognition site and the digestion site are preferably close to each other. Additionally, the term "activated protease" means a protease with an activity, and thus, the protease may be or may not be at an inactive state.

The term "substrate peptide for a protease" means a peptide comprising an amino acid sequence of a protein, which is recognized with the activated protease as a digestion site of the protein.

In one embodiment of the invention, the activated protease indicator is an indicator for monitoring protease activation.

The invention, furthermore, provides an expression vector expressing the activated protease indicator in vitro or in cells, which includes a DNA encoding Luc-C, a DNA encoding Luc-N, a DNA encoding the substrate peptide, a DNA encoding a C-half fragment of intein (Int-C) and a DNA encoding an N-half fragment of intein (Int-N) in an expression cassette thereof.

The expression vector allows for the expression of the indicator in vitro or in living cells. In the expression cassette of the expression vector, a DNA encoding Int-N and a DNA encoding Int-C are individually linked to the two ends of the chimeric DNA encoding "Luc-C/substrate peptide/Luc-N"; when fusion proteins are expressed from the expression cassette under appropriate conditions in vitro or in living cells, "Luc-C/substrate peptide/Luc-N" is cleaved out upon the protein splicing with Int-N and Int-C, and the C-terminal amino acid residue of Luc-N and the N-terminal amino acid residue of Luc-C are bound together with a peptide bond, to be a circular form.

As a specific embodiment of the expression vector, a DNA encoding Int-C, a DNA encoding Luc-C, a DNA encoding a substrate peptide, a DNA encoding Luc-N and a DNA encoding Int-N are linked together in this order along the 5' to 3' direction in the expression cassette thereof.

Herein, Int-C and Int-N are half fragments prepared by splitting one intein into two fragments at an appropriate site. The term "half fragment" means a state that intein is split at an appropriate site such that when the Int-C and Int-N coexist, these fragments can get the activity for protein splicing.

In a preferable embodiment of the expression vector, a DNA encoding PEST sequence is linked to the 5' or 3' side in the expression cassette. In case of PEST sequence being added, a linear fusion protein without protein splicing are rapidly decomposed with PEST sequence, so that only the circular form indicator comprising intein and the substrate peptide can exist in cells.

In accordance with the invention, the term "living cells" means cells placed in an artificial environment in which at least a part of the essential functions can be retained (for example, culture cells), or means cells in animals, which retain a part of the essential functions. In the latter, living cells with the indicator may compose a part or the entirety of an individual.

In one embodiment of the invention, the expression vector expresses an indicator for monitoring protease activation.

The invention further provides methodology for detection of activated protease in an in vitro assay system or in a cell, comprising introducing the activated protease indicator in the in vitro assay system or in the cell, and measuring a signal of activated luciferase generated upon the degradation of the substrate peptide.

Herein, the in vitro assay system includes for example any appropriate buffers or cell extracts containing a luciferase substrate, in which there is no limitation to buffer type, salt or pH, as long as the assay system is under a condition to allow for the exertion of the enzyme activities of the protease and the luciferase.

In the method for detecting an activated protease in cells, the activated protease indicator may be introduced in cells, by introducing the said expression vectors in the cells and then expressing an activated protease indicator finally circularized by protein splicing with intein from the expression vector.

As described above, the indicator of the invention emits luminescence signal from a luciferase in case that a specific activated protease exists. By introducing the indicator into an in vitro assay system or in living cells, the presence or absence of luminescence signal or its enhancement or attenuation can be used as a marker to detect an activated protease.

Because the level of the activated protease is in a proportional relation with the intensity of the luminescence signal in a given range, the activated protease can be quantitatively assessed, as well as be detected in an in vitro assay system or in cells. Thus, the method for quantitative assessment of the activated protease is also included in one embodiment of the invention.

Regardless of whether a protease has an inactive state or an activated state caused by an extraneous signal, the indicator of the invention can detect only the activated protease, and hence the indicator can monitor the activation of protease by means of a signal generated when the inactive protease is activated. Such method for detecting activation of protease is also encompassed in an embodiment of the invention.

The invention further provides a method for screening a factor effecting on protease activation in an in vitro assay system or in a cell, comprising introducing the activated protease indicator of claim 1 in an in vitro assay system or in a cell containing inactivated protease and/or activated protease, putting a candidate factor in contact with the an vitro assay system or with the cell, measuring a signal from activated luciferase upon degradation of the substrate peptide, before and after the contact with the candidate factor, and determining that the candidate factor is a protease-activating factor when the signal is increased, and that the candidate factor is a protease-inactivating factor when the signal is decreased.

In one embodiment of the method for screening for such factor in cells as described above, the activated protease indicator is introduced into the cell by introducing the expression vector in the cell thereby expressing the activated protease indicator from the expression vector, which indicator is finally circularized by protein splicing with an intein. In another embodiment thereof, additionally, the cells are eukaryotic cells or cells of animals.

The indicator of the invention emits luminescence signal from luciferase when the specific protease is activated. By introducing the indicator in an in vitro assay system or in living cells, and using the presence or absence of the luminescence signal or the enhancement or attenuation thereof as an index, it can be determined whether various factors introduced in the in vitro assay system or various factors contacted with cells are protease-activating factors or protease-inactivating factors. The term "factor" in this case includes for example environmental factors or intrinsic or extrinsic proteins, which may influence the activation of a specific protease in living cells, or includes for example drug candidate substances with a pharmacological mechanism of protease activation or inactivation.

Other terms and concepts of the invention are described in more detail in the description "Modes for Carrying out the Invention" or in "Examples". Additionally, the terms are essentially based on IUPAC-IUB Commission on Biochemical Nomenclature or are based on the meanings of such terms used in the technical field. Various techniques for use in carrying out the invention are readily and securely practiced by persons skilled in the art, on the basis of known references, except the techniques for which the references are cited by specific reference. For example, genetic engineering and molecular biology approaches are carried out by methods described in for example J. Sambrook, E. F. Fritsch & T. Maniatis, "Molecular Cloning: A Laboratory Manual (2nd edition)", Cold Spring Harbor Laboratory Press, Cold Spring Harbor, New York (1989); D. M. Glover et al. eds., "DNA Cloning", 2nd edition, Vol.1 to 4, (The Practical Approach Series), IRL Press, Oxford University Press (1995); Ausubel, F. M. et al., Current Protocols in Molecular Biology, John Wiley & Sons, New York, N.Y., 1995; "Zoku Seikagaku Jikken Koza (Biochemical Experimental Lecture Series, Supplementary) 1, Idensi Kenkyu-ho (Genetic Engineering Research Approach) II", Nippon Sei-Kagaku Gakkai (The Japanese Biochemical Society) eds., Tokyo Kagaku Dojin (1986); "Shin Seikagaku Jikken Koza (New Biochemical Experimental Lecture Series) 2, Kakusan (Nucleic Acid) III (Kumikae DNA Gijyutu (Recombinant DNA Technique))", Nippon Sei-Kagaku Gakkai (The Japanese Biochemical Society) eds., Tokyo Kagaku Dojin (1992); R. Wu ed., "Methods in Enzymology", Vol.68 (Recombinant DNA), Academic Press, New York (1980); R. Wu et al., ed., "Methods in Enzymology", Vol. 100 (Recombinant DNA, Part B) & 101 (Recombinant DNA, Part C), Academic Press, New York (1983); R. Wu et al. ed., "Methods in Enzymology", Vol. 100 (Recombinant DNA, Part B) & 101 (Recombinant DNA, Part C), Academic Press, New York (1983); R. Wu et al. ed., "Methods in Enzymology", Vol. 153 (Recombinant DNA, Part D), 154 (Recombinant DNA, Part E) & 155 (Recombinant DNA, Part F), Academic Press, New York (1987) or methods described in references cited in those described above or methods substantially identical to those described above or modified methods of them. Additionally, various proteins, peptides or DNAs encoding them are available on the existing database.

Furthermore, the invention encompasses the contents disclosed in JP-A-2004-108943; JP-A-2004-104222; JP-A-02-088766; and WO2005/085439, all of which relate to the reconstruction of reporter molecules through protein splicing.

The present application claims priority based on Japanese Patent Application 2007124924 filed on the date of May 9, 2007, and encompasses the contents thereof in the present specification by reference to the specification of the Japanese Patent Application.

BEST MODE FOR CARRYING OUT THE INVENTION

The activated protease indicator of the invention is a circular form comprising the C-terminal half of luciferase (Luc-C) and the N-terminal half of luciferase (Luc-N) linked together through a substrate peptide for a protease.

The luciferase may be, for example, the known types of luciferases including *Photinus pyralis* (firefly) luciferase, *Renilla* (*Renilla reniformis*) luciferase, click beetle (*Pyrophorus plagiophthalamus*) luciferase, and *Gaussia* (*Gaussia princeps*) luciferase. The amino acid sequences and the nucleotide sequences of the genes (cDNAs) encoding these luciferases are known (for example, those of firefly luciferase and click beetle luciferase can be known as GenBank/AB062786 and GenBank/AY258592-1, respectively). With reference to known information of sequences, the sites to be split into two fragments can appropriately be determined. The firefly luciferase (Fluc), for example, may be split at the sites of the amino acids 415/416, as described in the following Examples. *Renilla* luciferase may be split at any appropriate site as described in a reference (Kim, S. B.; Ozawa, T.; Watanabe, S.; Umezawa, Y., Proc. Natl. Acad. Sci. USA, 2004, 101, 11542-7). Particularly, splitting at the amino acids 91/92 makes luminescence intensity after reconstruction highest. Further, click beetle luciferase (CBLuc) may be split at the site of the amino acids 439/440 or the amino acids 412/413 or the like into two fragments.

Regarding these luciferases, the N-half fragment and the C-half fragment with a partial overlap or deletion may be used.

The substrate peptide for a protease comprises an amino acid sequence specifically recognized by a target protease. In case of caspase being the target protease, for example, the amino acid sequence of the substrate peptide for caspase-3 is Asp-Glu-Val-Asp (DEVD). For caspase-8, the amino acid sequence is Leu-Glu-Thr-Asp (LETD); for caspase-9, the amino acid sequence is Leu-Glu-His-Asp (LEHD). The substrate sequence for calpain I and calpain II is Leu-Leu-Val-Tyr (LLVY). It is needless to say that the substrate peptide of the invention is never limited to the examples described above, and that an appropriate substrate peptide can be selected depending on the target protease for detecting the activation. For example, the sequence information of substrate peptides for proteases is readily available on the existing database. A substrate peptide may satisfactorily be the sequence itself recognized by a protease, or may contain one or plural optional amino acid residues before and/or after the recognition sequence.

To express such indicator in living cells, the expression vector of the invention is used. The expression vector carries in the expression cassette "DNA encoding Luc-C", "DNA encoding Luc-N", "DNA encoding a substrate peptide", "DNA encoding the intein C half fragment (Int-C)" and "DNA encoding the intein N half fragment (Int-N)".

Figure 1:
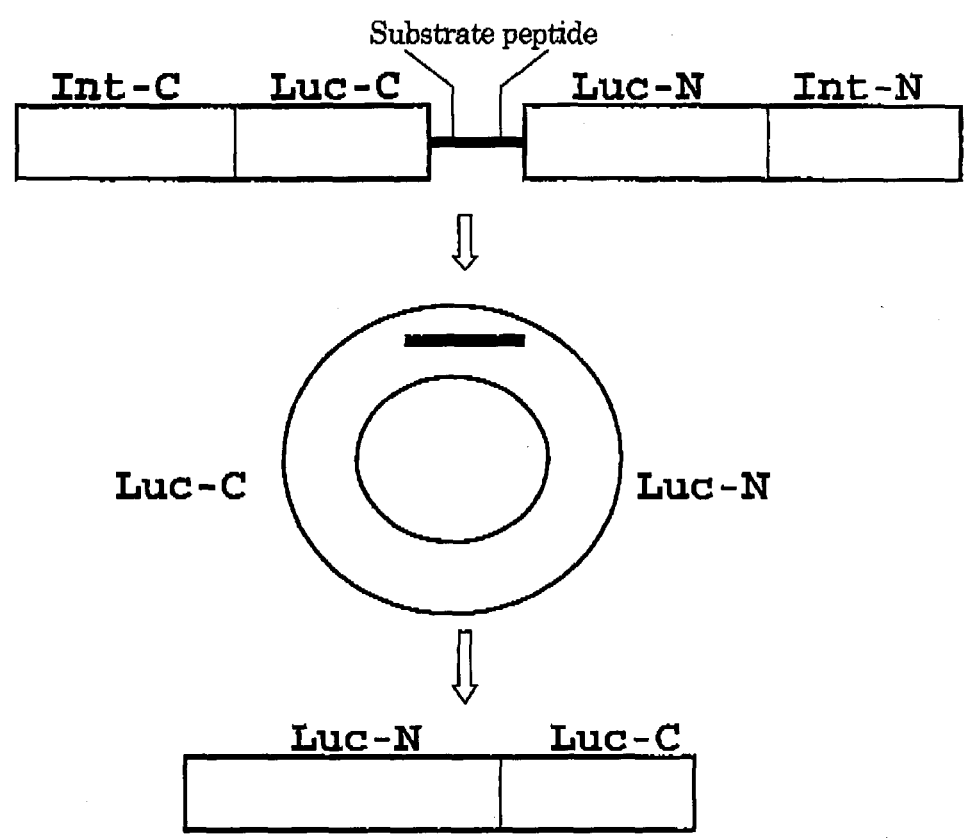
[FIG. 1(A)] The fundamental principle of the activated protease indicator of the invention; the upper column shows the fusion protein [Int-C/Luc-C/substrate peptide/Luc-N/Int-N] expressed from the expression vector; the middle column shows the indicator in the circular form, as excised by protein splicing with intein; the lower column shows luciferase [Luc-N/Luc-C] falling into the linear form upon digestion of the substrate peptide with protease, to restore the luminescence function.
[FIG. 1(B)] Principle for monitoring the activity of caspase-3 by using cyclic firefly luciferase (Fluc). With the protease substrate (DEVD), the C-terminal fragment of Fluc (Fluc-C) is linked to the N-terminal fragment of Fluc (Fluc-N). The C- and N-terminal fragments of DnaE (DnaEc and DnaEn) are linked to the two ends of Fluc. So as to decompose purified products without protein splicing, PEST sequence is arranged onto the C terminus. In case of a fusion protein being expressed in cytoplasm, DnaEc interacts with DnaEn for protein splicing, leading to the consequent generation of inactive cyclic Fluc. In case that caspase-3 is activated in cytoplasm, caspase-3 digests out the DEVD sequence to restore the Fluc activity.
Figure 1:
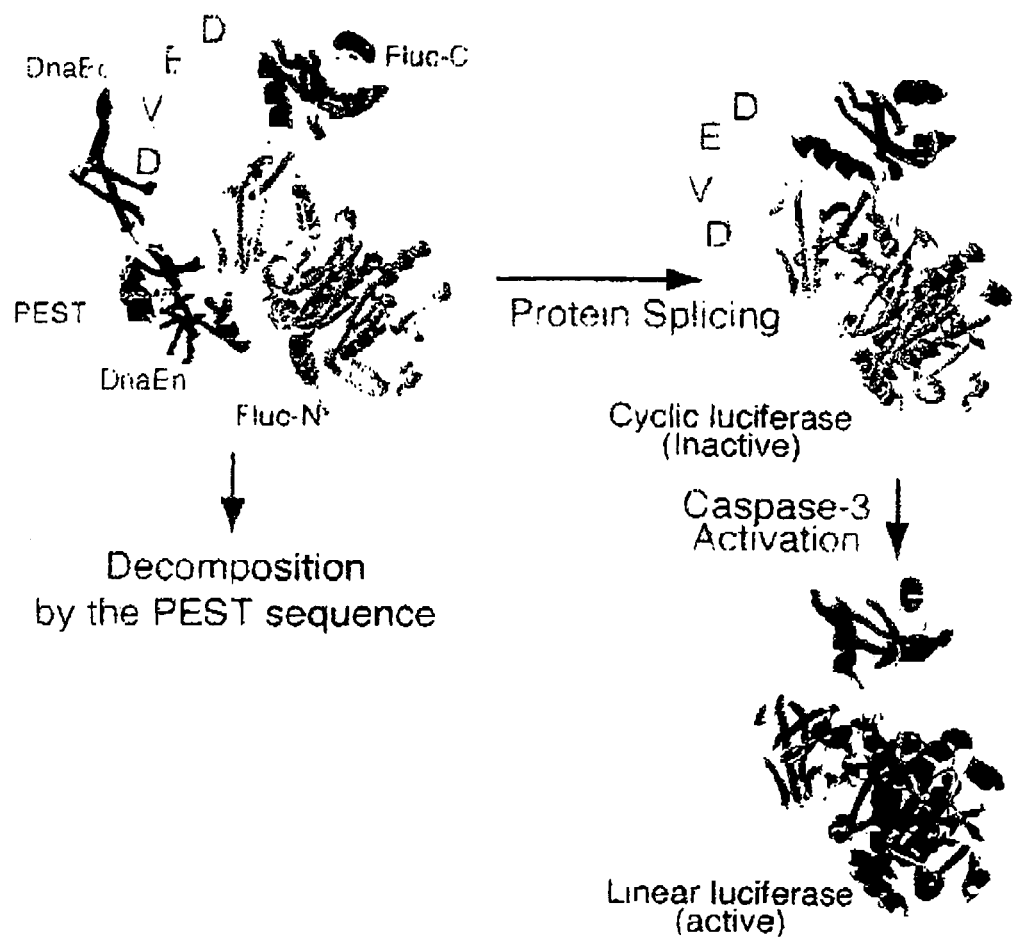

The expression vector expresses a fusion protein "Int-C/Luc-C/substrate peptide/Luc-N/Int-N" as listed in the upper column of FIG. 1(A). When the fusion protein is expressed in living cells, a fusion protein "Luc-C/substrate peptide/Luc-N" is cleaved by the protein splicing with Int-C and Int-N, leading to the construction of a circular form as shown in the middle column of FIG. 1(A). Then, the C-terminus of Luc-N and the N-terminus of Luc-C are bound together by a peptide bond. Because the fusion protein is in a steric structure of a distorted circular form, the bound Luc-N/Luc-C does not have any luminescence function. When the indicator coexists with the protease, the protease digests out the substrate peptide. As shown in the lower column of FIG. 1(A), Luc-N/Luc-C falls into a linear form and resolves the distortion, so that Luc-N/Luc-C is reconstructed as luciferase with the luminescence function. The reconstructed luciferase emits luminescence signal in the presence of luciferin as the substrate for the luciferase.

The intein derived from yeast VMA or DnaE intein derived from cyanobacteria may be listed, without limitation. From the existing intein database, necessary sequence information and the splitting positions may be available for use in accordance with the invention.

Further, "PEST sequence" may effectively be fused with any one of the ends of the fusion protein "Int-C/Luc-C/substrate peptide/Luc-N/Int-N". The PEST sequence is abundant in proline, glutamic acid, serine and threonine. Intracellular decomposition of proteins containing the PEST sequence is promoted. An appropriate PEST sequence may be used with reference to the descriptions in references [Rogers, S. et al. (1986) Science. 234, 364-8; Ghoda L. et al. (1989) Science. 243, 1493-5; Rechsteiner, M. & Rogers, S. (1996) Trends Biochem. Sci. 21, 267-71].

Any known vectors (vectors for eukaryotic cells) may be used, without any specific limitation, as a base vector for the expression vector of the invention. The individual DNAs as elements of the expression cassette can be obtained from cDNA libraries, using probes prepared on the basis of individual known nucleotide sequence information or can be obtained by PCR or RT-PCR using primers prepared on the basis of sequence information. The DNA encoding the substrate peptide can be synthetically prepared in vitro by well-known chemical synthesis techniques, such as those described in references [Carruthers (1982) Cold Spring Harbor Symp. Quant. Biol. 47:411-8; Adams (1983) J. Am. Chem. Soc. 105: 661; Belousov (1997) Nucleic Acids Res. 25:3440-4; Frenkel (1995) Free Radical Biol. Med. 19:373-80; Blommers (1994) Biochemistry 33: 7886-96; Narang (1979) Methods Enzymol. 68:90; Brown (1979) Methods Enzymol. 68:109; Beaucage (1981) Tetrahedron Lett. 22: 1859; U.S. Pat. No. 4,458,066].

So as to control the expression of the fusion protein (for example, the expression in a specific tissue in a living organism), a known tissue-specific promoter sequence may be integrated in the expression vector.

Such expression vector can be introduced in cells by known transfection methods such as microinjection and electroporation. Otherwise, intracellular introduction methods with lipids [BioPORTER (manufactured by Gene Therapy Systems, USA), Chariot (Active Motif Corporation, USA)] may also be used. The expression vector of the invention may also be constructed as a viral vector for introducing the indicator into living cells. Such viral vector includes for example retrovirus vector suitable for gene introduction into mammalian cells or mammal individuals, vectors based on human immunodeficiency virus (HIV), lentivirus vector, adenovirus vector, adeno-associated virus vector, herpes virus vector and vaccinia virus vector (see for example Miller et al. Bio Techniques 7:980-90, 1992; Anderson et al. Nature 392: 25-30 Suppl., 1998; Verma and Somia, Nature 389: 239-42, 1997; Wilson, N. Engl. J. Med. 334:1185-87, 1996). In case that the method of the invention is used for animals, a transgenic animal carrying the expression vector in the genome may be prepared to introduce the expression vector genetically from cells of the parent animal to cells of the progeny animal.

The expression vector carrying a promoter for in vitro transcription, such as T7 promoter and SP6 promoter, can work in known in vitro transcription systems. By translating the resulting mRNA in an in vitro translation systems with wheat germ extract etc., the fusion protein "Int-C/Luc-C/substrate peptide/Luc-N/Int-N" as shown in the upper column of FIG. 1(A) can be obtained. Through the in vitro protein splicing with Int-C and Int-N, further, the circular peptide shown in the middle column of FIG. 1(A) can be prepared. By purifying the circular peptide by known methods, the resulting circular peptide can be used as the activated protease indicator.

The method for detecting activated protease in accordance with the invention comprises introducing the activated protease indicator in an in vitro assay system or in cells and determining the signal from activated luciferase as generated upon the decomposition of the substrate peptide.

For introducing the activated protease indicator in the in vitro assay system, the activated protease indicator may be isolated and added to the system. For isolating the activated protease indicator, the expression vector may be introduced in cells; the indicator, which is finally circularized through the protein splicing with intein, may be expressed from the expression vector, and subsequently, the indicator may satisfactorily be purified from the cells by known methods; as described above. Alternatively, transcription, translation and protein splicing in vitro may be done, and then, the resulting indicator may be purified.

For introducing the activated protease indicator in cells, the expression vector may be introduced in cells, to express the finally circularized indicator through the protein splicing with intein from the expression vector. Using a transmembrane peptide, alternatively, the "Int-C/Luc-C/substrate peptide/Luc-N/Int-N" synthetically prepared in vitro may be introduced in cells to induce protein splicing. In this case, the expression vector should be constructed so as to allow for the removal of the transmembrane peptide, simultaneously with the splicing.

Any known methods appropriate for the system may be selected as the method for detecting luciferase activity. In case of an assay system in vitro, for example, luciferin is added as the substrate to the assay system, for detection with a luminometer. In case of culture cells, luciferin is added to the culture medium, for detection with a photon counter. In case of an animal, luciferin is intravenously or intraperitoneally administered to the animal, for detection of the luminescence with a stereoscopic microscope equipped with a CCD camera.

As the activated protease indicator of the invention can detect the activated protease, it can also detect the event of protease activation from the inactive type to the active type on real time. In accordance with the present specification, the indicator for detecting protease activation is referred to as indicator of protease activation.

The screening method in accordance with the invention comprises a first step of introducing the indicator of protease activation in an in vitro assay system or in cells containing inactivated protease and/or activated protease. The introduction can be done in the same manner as in the case of the method described above. By subsequently putting a candidate factor in contact with the in vitro assay system or with the cells, the signal of activated luciferase upon the decomposition of the substrate peptide with a protease is determined before and after the contact of the candidate factor. In case that the signal is enhanced after the contact compared with the signal before the contact, the candidate substance is determined as a protease-activating factor. In case that the signal is attenuated after the contact compared with the signal before the contact, the candidate substance is determined as a protease-inactivating factor.

The candidate factor as the subject for the screening method includes any substances potentially influencing the activation or inactivation of a protease in an in vitro assay system or in living cells. In case of an in vitro assay system, a factor influencing the protease activity itself may possibly be identified, mainly. In case of living cells, a factor indirectly influencing the protease activity itself may possibly be identified as well. The candidate factor includes for example factors influencing the signal transduction system controlling the protease activity.

The screening subjects for the method may also be active components for therapeutic drugs for various diseases caused by protease activation or inactivation. Specifically, as protease is closely involved in cell apoptosis, inappropriate apoptosis causes a great number of diseases such as Alzheimer's disease, Huntington's disease, ischemia, autoimmune disease, and immortalization of cancer cells. Therefore, the high-precision assay of the influence of a drug candidate substance or an active component thereof on protease activity in living cells makes great contributions to the development of an effective therapeutic drug.

The candidate factor as the screening subject includes for example organic or inorganic compounds (low-molecular compounds, in particular), proteins and peptides. These substances may possess known or unknown functions or structures. Additionally, the "combinatorial chemical library" is an effective potential tool as a substance group to be tested for identifying a target substance efficiently. The preparation and screening of such combinatorial chemical library is well known in the art (see for example U.S. Pat. Nos. 6,004,617; and 5,985,365). Additionally, commercially available such libraries (for example, libraries manufactured by ComGenex, USA; Asinex, Russia; Tripos, Inc., USA; ChemStar, Ltd., Russia; 3D Pharmaceuticals, USA; Martek Biosciences, USA) may be used alike. By applying the combinatorial chemical libraries to a cell population expressing the indicator, so-called "high-throughput screening" may also be achieved.

A kit for detecting activated protease of the invention includes any of the activated protease indicators or any of the expression vectors as described above. With the kit, an activated protease can readily be detected. The detection method is as described above. In addition to the activated protease indicator or the expression vector, the kit may satisfactorily include those for detecting activated protease, such as a buffer, a substrate for luciferase (luciferin), and an instruction manual. Additionally, the kit may be used as a kit for detecting protease activation or a screening kit for use in the screening method described above.

The invention is now specifically described in more detail with reference to Examples. However, the invention is never limited by the following Examples.

EXAMPLE 1

1. Method
1-1. Construction of Plasmid

Using the *Escherichia coli* strain DH5-α as a host, all plasmids were constructed. By PCR, an initiation codon and enzyme sites BamH I and Mun I were individually introduced in cDNA of the C-terminal fragment of DnaE. Using the Sal I site, cDNA of the C-terminal fragment (399-550 aa) of Fluc was conjugated to cDNA of the N-terminal fragment (2-416 aa) of Fluc, and subsequently, the Mun I and Hind III sites were independently introduced in the 5' and 3' termini, respectively of the resulting chimera DNA. By PCR, the PEST sequence and enzyme sites Hind III and Xho I were introduced in cDNA of the N-terminal fragment of DnaE. The resulting PCR products were sequenced with a DNA sequencer ABI prism 310 (Applied Biosystems, Tokyo, Japan), to determine the fidelity. These fragments were conjugated together, for subcloning into the BamH I site and Xho I site of an expression vector pcDNA 3.1 (+) (Invitrogen, Carlsbad, Calif.). Caspase-3 cDNA was kindly supplied by Dr. Ryosuke Takahashi (RIKEN BSI, Japan). pRL-TK was available from Promega Co. (Madison, Wis.). pX8luc was constructed according to the report (Kanno, A. et al. (2006) Anal. Chem. 78, 556-60).

1-2. Cell Culture and Transfection

HeLa and COS-7 cells were cultured in the Dulbecco's modified Eagle's medium (Gibco BRL, Rockville, Md.) supplemented with 10% fetal bovine serum (FBS) (Gibco BRL) and 1% penicillin/streptomycin (Gibco, BRL), under conditions of 5% $CO_2$ and 37° C. MCF-7 cells were cultured in the Eagle's minimum essential medium (Gibco BRL) supplemented with 10% FBS, 1% penicillin/streptomycin, 1 mM sodium pyruvate (Gibco, BRL) and the 0.1 mM non-essential amino acid solution (Gibco BRL), under conditions of 5% $CO_2$ and 37° C. cDNA was transfected in cells, using the TransIT-LT1 reagent (Minis Bio Co. Madison, Wis.).

1-3. Western Blot Analysis pcFluc-DEVD was transfected in the COS-7 cells for 48 hours. The cells were stimulated with staurosporine (STS; Sigma, St. Louise, Mo.) and then disrupted in a lysis buffer (1% SDS, 10% glycerol, 10% 2-mercaptoethanol, 0.001% Bromophenol Blue, 50 mM Tris/HCl, pH 6.8). The sample was electrophoresed with 10% SDS polyacrylamide gel, which was then transferred on a nitrocellulose membrane (Hybond-ECL, GE Healthcare, Buckinghamshire, England). Fluc was detected with a polyclonal anti-luciferase antibody (Promega); the immunoreactivity was evaluated, using horseradish peroxidase (HRP) conjugated to an anti-goat IgG antibody (Promega). The HRP activity was visualized, using an ECL advance Western blotting detection kit (GE Healthcare) with LAS-1000 plus image analyzer (Fuji Film Co., Tokyo, Japan).

1-4. In vitro Assay of Firefly Luciferase pcFluc-DEVD and pRL-TK were transfected in the COS-7 cells and the HeLa cells for 48 hours. These cells were treated with STS or a caspase inhibitor Z-VAD-FMK (Sigma) to assay the luciferase activity according to the report (Ozawa, T. et al. (2001) Anal. Chem. 73, 2516-21; Kanno, A. et al. (2006) Anal. Chem. 78, 556-60). The assay time period of Fluc and *Renilla reniformis* luciferase (Rluc) was 20 seconds. The luminescence from Fluc ($L_F$) was normalized to the luminescence from Rluc ($L_R$), and the resulting value was defined as relative luminescence unit (RLU; $RLU=L_F/L_R$). All the assays were done in various wells in a culture plate triplicately, using a luminometer of MiniLuraat LB9506 (Berthold GmbH & Co. KG, Wildbad, Germany). The results are shown as the mean ratio of the RLU value to the RLU value of cells treated with a solvent (0.1% DMSO), together with the standard deviations.

1-5. Luciferase Activity Over Time pcFluc-DEVD was transfected in the HeLa cells in a 10-cm Petri dish for 24 hours. The cells were scraped off and divided in five 3-cm Petri dishes, for culturing for 24 hours. The culture medium was replaced with the Hank's balanced salt solution (Gibco) containing 500 μM D-luciferin and 5% FBS. After the five 3-cm Petri dishes were mounted on a photon counter (KRONOS, ATTO, Tokyo, Japan), the cells were stimulated with STS or actinomycin D (Act D, Sigma). The luminescence intensity in each of the Petri dishes was assayed for a cumulative time period of 45 seconds at an interval of 5 minutes.

1-6. In vivo Imaging of Caspase Activity in Living Mice pX8luc or pcFluc-DEVD was transfected in HeLa cells for 48 hours. The cells were harvested and suspended in a phosphate buffered saline (PBS), from which $1.0 \times 10^6$ cells were transplanted in two different dorsal positions of a BALB/c-nude mouse (female, five-week-old, body weight of about 17 to 20 g). After the cell transplantation, STS dissolved in DMSO was intraperitoneally injected. Immediately thereafter, a PBS buffer containing D-luciferin (600 mg/kg body weight) was intraperitoneally injected, to assay the luminescence from the mouse, using a CCD camera (IVIS200 system, Xenogen, Alameda, Calif.). Photons emitted from the transplanted cells were counted and cumulatively recorded over one minute. Image analysis was done, using the software LIVING IMAGE (Xenogen). So as to quantitatively determine the assayed luminescence, a region of interest was extracted from the cell-transplanted regions, to evaluate the luminescence intensity ($photon \cdot second^{-1} \cdot cm^{-2}$).

Figure 2:
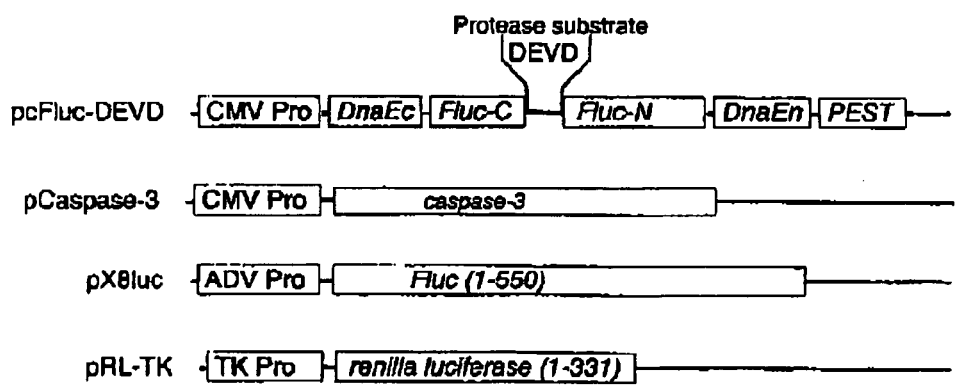
[FIG. 2] Schematic structures of the cDNA constructs. Italic letters are the genes of corresponding proteins. Pro means a promoter.

2. Results
2-1. Design of Circular Luciferase for Use in Detecting Caspase-3 Activity The crystal structure of Fluc indicates that luciferase folds into two compact domains, a large N-terminal domain and a small C-terminal one (FIG. 1(B)) (Conti. E. et al. (1996) Structure, 4, 287-98). These domains are separated by a wide cleft, in which the active center of Fluc is located. The N- and C-terminal ends of Fluc visible in the crystal structure are not in close proximity (the distance between residue Asp-3 and Lys-544 is about 4 nm). Both the N- and C-termini of Fluc locate on the same side on the behind of the active center. In the Example, it was understood on the basis of the structural information about Fluc that linkage of the N- and C-terminal ends of Fluc by the substrate sequence of caspase-3, DEVD, results in great attenuation the Fluc activity. In order to connect the N-terminal end with the C-terminal one, herein, naturally split DnaE intein derived from *Synechocystis* sp. PCC6803 (Wu, H. et al. (1998) Proc. Natl. Acad. Sci. USA, 95, 9226-31) was chosen, because previous reports have indicated that this DnaE intein gives cyclic peptides and proteins in high yield (Scott, C. et al. (1999) Proc. Natl. Acad. Sci. USA, 96, 13638-43; Scott, C. P. et al. (2001) Chem. Biol. 8, 801-15; Nichols N. M. & Evans, T. C., Jr. (2004) Biochemistry 43, 10265-76; Evans, T. C. Jr. et al. (2000) J. Biol. Chem. 275, 9091-4). The C- and N-terminal fragments of DnaE were connected with the C- and N-terminal ends of the luciferase, respectively (FIG. 2). In addition, PEST sequence, which is known to accelerate degradation of a protein (Rogers, S. et al. (1986) Science. 243, 364-8; Ghoda, L. et al. (1989) Science.

243, 1493-5) was attached to the C-terminal end of the fusion DNA. The PEST sequence results in the degradation of only unspliced products of protein splicing, because cyclic Fluc does not possess the PEST sequence. Consequently, only cyclic Fluc accumulates inside the cells. If caspase-3 is activated in cells expressing the cyclic Fluc, the cyclic Fluc is changes into an active form and its luminescence activity is restored. Thus, cells expressing cyclic Fluc allow monitoring of caspase-3 activity with luminescence signals.

Figure 3:
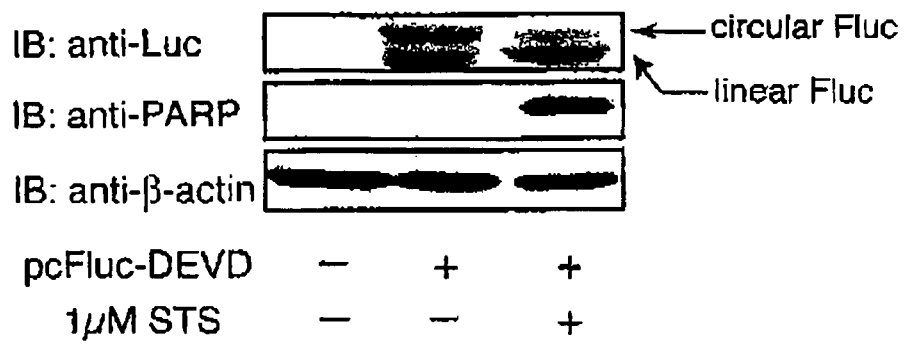
[FIG. 3] Western blot analysis of COS-7 cells transfected with pcFluc-DEVD for 48 hours. The cells were treated with 1 µM staurosporine (STS) for two hours and harvested. The activity of caspase-3 was evaluated from the digested PARP with an anti-PARP antibody. As a reference for the amounts of the proteins in the electrophoresis, β-actin was stained with its specific antibody.
Figure 4:
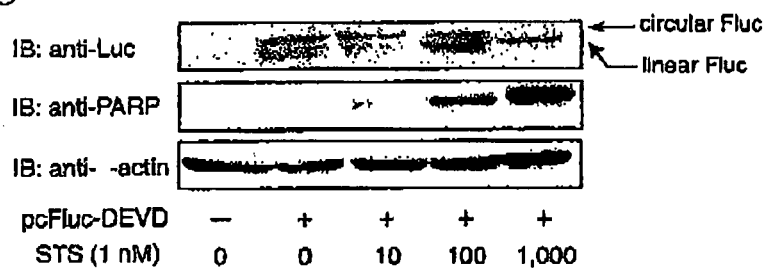
[FIG. 4] Western blot analysis of Fluc in the circular form and in the linear form. COS-7 cells transfected with pcFluc-DEVD for 48 hours were treated with the indicated concentrations of STS for two hours and harvested. The sample was electrophoresed, transferred on a nitrocellulose membrane and stained with a specific antibody.

2-2. Functional Assessment of Circular Firefly Luciferase for Use in Detecting Caspase-3 Activity To assess whether the fusion protein expressed by pcFluc-DEVD produces cyclic Fluc by protein splicing, herein, pcFluc-DEVD was transfected in COS-7 cells and chimera proteins were transiently expressed for 48 hours. The spliced products were examined by Western blot (FIG. 3). For inducing the apoptosis, herein, staurosporine (STS) was used for an apoptosis-inducing reagent, which triggers the digestion of the DEVD amino acid sequence by caspase-3. Caspase-3 activity in cells was confirmed by blotting a poly(ADP-ribose) polymerase (PARP) that contains a DEVD sequence. In lysates of the cells in the absence of STS, the luciferase antibody recognized two components near to 60 kDa; the molecular weight of the major product, corresponding to the cyclic Fluc, is higher than that of the other product. In the presence of STS, the luciferase antibody strongly recognized the lower product, which corresponds to a linear form of Fluc, whereas the intensity of the product with higher molecular weight was very weak. Formation of the linear form of Fluc was dependent on the concentration of STS (FIG. 4). The results indicate that the linear form of Fluc was generated by the activation of caspase-3 and that the DEVD sequence incorporated in the cyclic form was digested.

Figure 5:
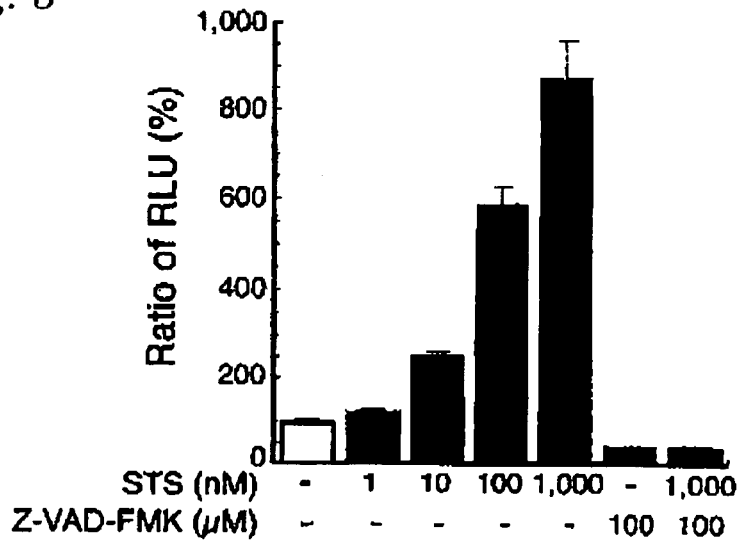
[FIG. 5] Quantitative analysis of the Fluc activity with STS and Z-VAD-FMK. After transfection of COS-7 cells with pcFluc-DEVD for 48 hours, the cells were treated with 100 µM Z-VAD-FMK or vehicle (0.1% DMSO) for an hour and then stimulated with various concentrations of STS for two hours. A relative luminescence unit (RLU) was defined as follows: the luminescence intensity from the right side (LumR) was divided by that from the left side (LumL), as RLU (%)=LumR/LumL.

In the Example, continuously, it was examined whether the activity of the cyclic Fluc was restored after stimulation with STS. COS-7 cells transfected with pcFluc-DEVD were stimulated with STS or a caspase inhibitor Z-VAD-FMK, or with both STS and Z-VAD-FMK. The cells were harvested and their lysates were mixed with a Fluc substrate, D-luciferin. The luminescence signals increased with increase in concentrations of the STS and the maximum response was strong enough to be discriminated from the signal in the absence of STS (FIG. 5). Cells with 100 µM Z-VAD-FMK showed no increase in luminescence in the presence or absence of 1 µM STS. The luminescence signals in the presence of Z-VAD-FMK were smaller than the signals that originated from the cells in the absence of STS and Z-VAD-FMK. This indicates that the unstimulated cells had slight caspase-3 activity.

Figure 6:
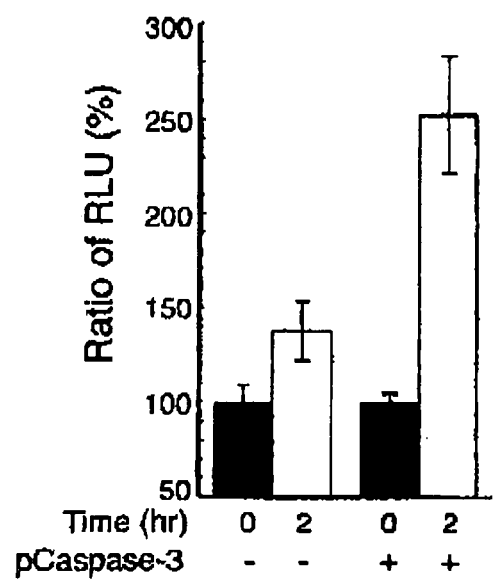
[FIG. 6] Analysis of the Fluc activity in the caspase-3-deficient MCF-7 cells. MCF-7 cells were transfected with only pcFluc-DEVD (left) or with both pcFluc-DEVD and pCaspase-3 (right). The cells were incubated for 48 hours and the luminescence intensities were evaluated at the indicated times after stimulation with 100 nM STS. A relative luminescence unit (RLU) was defined as follows: the luminescence intensity from the right side (LumR) was divided by that from the left side (LumL), as RLU (%)=LumR/LumL.

To provide evidence that digestion of the cyclic Fluc was indeed mediated by caspase-3, the caspase-3-deficient MCF-7 cells (Janicke, R. U. et al. (1998) J. Biol. Chem. 273, 9357-60) were used. When cells transfected with pcFluc-DEVD were stimulated with 1 µM STS for two hours, little change in the bioluminescence intensity was observed (FIG. 6). By contrast, when MCF-7 cells were cotransfected with pcFluc-DEVD and pCaspase-3 the luminescence from the cells significantly increased upon stimulation with STS. From these result, it was concluded that inactive cyclic Fluc was created by protein splicing inside the cells and the activity of Fluc was restored when caspase-3 digested the DEVD sequence.

Figure 7:
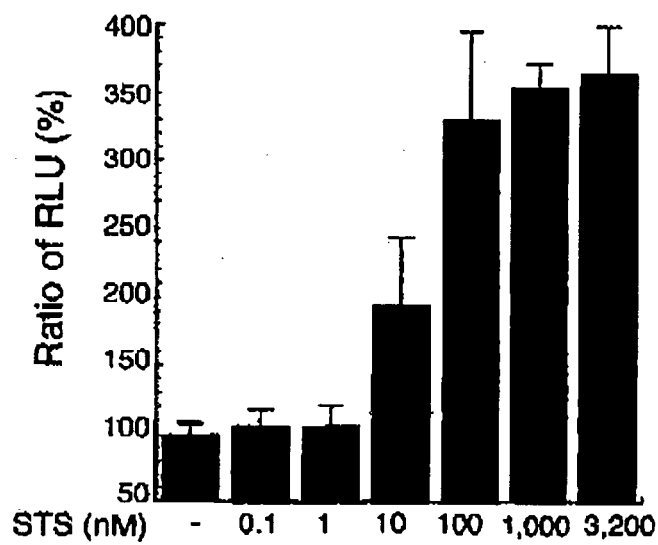
[FIG. 7] Quantitative analysis of the Fluc activity with STS. After transfection of HeLa cells with pcFluc-DEVD for 48 hours, the cells were treated with various concentrations of STS for two hours. A relative luminescence unit (RLU) was defined as follows: the luminescence intensity from the right side (LumR) was divided by that from the left side (LumL), as RLU (%)=LumR/LumL.
Figure 8:
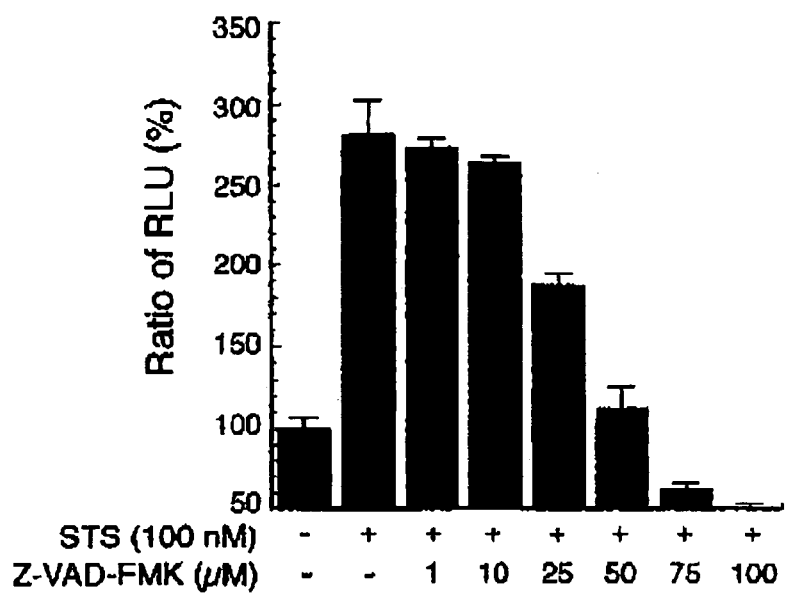
[FIG. 8] Quantitative analysis of the Fluc activity with Z-VAD-FMK. The HeLa cells were transfected with pcFluc-DEVD for 48 hours, treated with different concentrations of Z-VAD-FMK or vehicle (0.1% DMSO), and stimulated with various concentrations of STS for two hours. A relative luminescence unit (RLU) was defined as follows: the luminescence intensity from the right side (LumR) was divided by that from the left side (LumL), as RLU (%)=LumR/LumL.

To show the feasibility of cyclic Fluc for characterizing apoptotic regents, the sensitivity of cyclic Fluc was examined, using HeLa cells. The cells were transfected with pcFluc-DEVD, for transient expression of chimera proteins, which were stimulated with different concentrations of STS for two hours. Then, it was revealed that STS induced an increase in the bioluminescence intensity at concentration range of $1.0 \times 10^{-8}$ to $1.0 \times 10^{-6}$ M (FIG. 7). Next, inhibitory effects on the caspase-3 activity were examined with a model caspase-3 inhibitor, Z-VAD-FMK (FIG. 8). The inhibitory effect of Z-VAD-FMK on the cleavage of the cyclic Fluc was observed at the concentrations of Z-VAD-FMK higher than 10 µM. With 100 µM Z-VAD-FMK, the cleavage of the cyclic Fluc was completely suppressed. These results indicate that the cells expressing cyclic Fluc can be used for quantitative analysis of apoptosis-inducting and -inhibiting chemical compounds in living cells.

2-3. Real-time in vitro Analysis of Caspase-3 Activity

Figure 9:
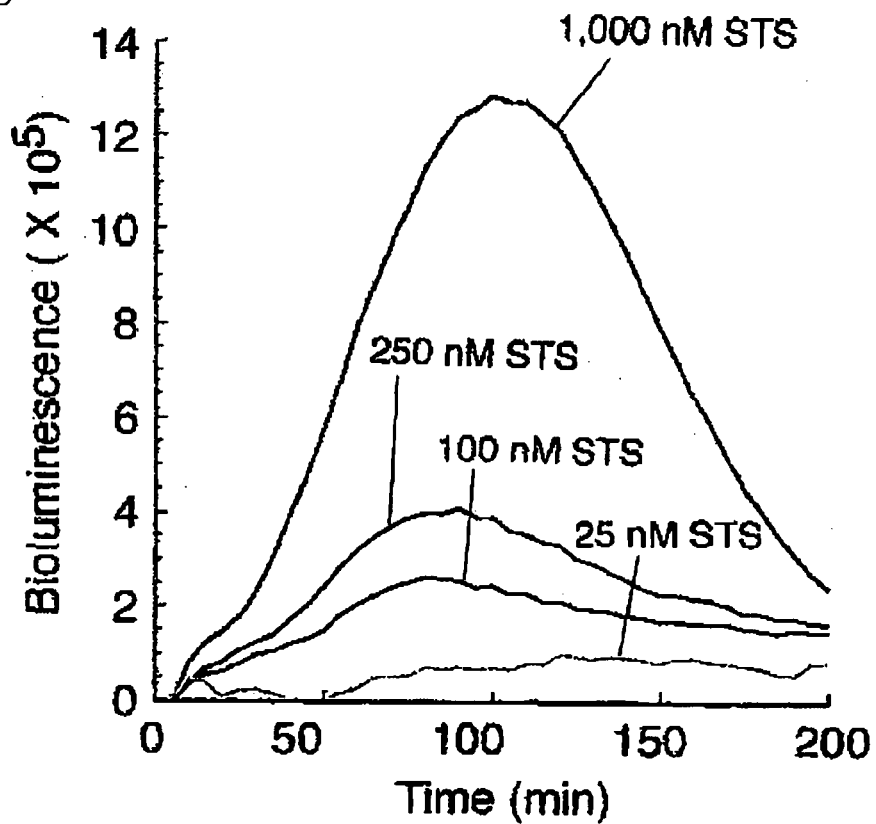
[FIG. 9] Real-time in vitro analysis of caspase-3 activity. Forty eight hours after HeLa cells transfected with pcFluc-DEVD were treated with different concentrations of STS and then the bioluminescence intensities were measured every 5 minutes. The indicated time represents the time after the addition of each agent.
Figure 10:
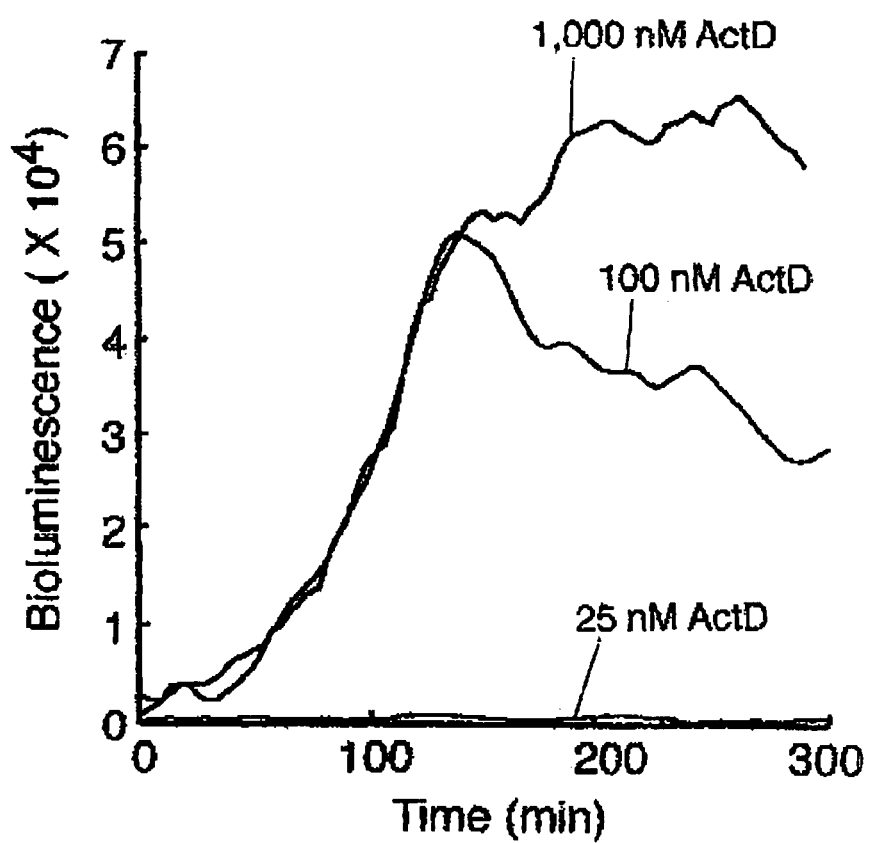
[FIG. 10] Results of the measurement with actinomycin D (ActD) in the same manner as in FIG. 9. Real-time in vitro analysis of capsase-3 activity. Forty eight hours after HeLa cells transfected with pcFluc-DEVD were treated with different concentrations of actinomycin D (ActD) and then the bioluminescence intensities were measured every 5 minutes. The indicated time represents the time after the addition of each agent.

It is known that the time required for caspase-3 activation in response to extracellular stimuli varies with the type of chemical compounds and its concentration. In order to decide upon a screening time, it is crucial to know when the activity of caspase-3 gives a maximum response after stimulation with such apoptotic chemical regents. In the Example, in the set of the following experiments, the real-time analysis of caspase-3 activity in living cells was performed. First, the cyclic Fluc indicator was transiently expressed in HeLa cells; the luminescence intensity upon stimulation with STS at various concentrations was monitored every five minutes in a time course (FIG. 9). The cells initially showed a slow increase in the luminescence signals for 25 minutes. The rate of increase in the luminescence intensity depended on the STS concentration. The luminescence signals were found to reach a maximum 100 minutes after stimulation with STS. It should be particularly described herein that the signals then gradually decreased. The decrease in the luminescence signal intensity indicates attenuation of active luciferase by proteolysis in the HeLa cells. When HeLa cells expressing the cyclic Fluc were stimulated with actinomycin (ActD) as a potential anti-cancer agent, the luminescence signal intensity similarly increased over the time period of 25-120 minutes and then gradually decreased (FIG. 10). These data indicate that the time to obtain maximal luminescence is approximately 120 minutes after stimulation with the chemical compounds and this is the most suitable time for high-throughput screening of chemical compounds.

2-4. Real-time in vivo Imaging of Caspase-3 Activity in Living Mice

To demonstrate a further application of cyclic Fluc, this reporter was applied to the investigation of the distribution of chemical compounds in organs of living mice and to the quantitation of their effects on caspase-3 activity. Attentions are generally focused on issues including an issue about whether chemical compounds and drug candidate compounds are delivered via blood circulation to target organs; an issue about whether compounds are enriched or metabolized in the organs when the mouse is exposed to the compounds; and an issue about whether the compounds in the target organs actually effect on the caspase-3 activity. Using the present bioluminescence imaging technique, the information thereabout can be obtained.

Figure 11:
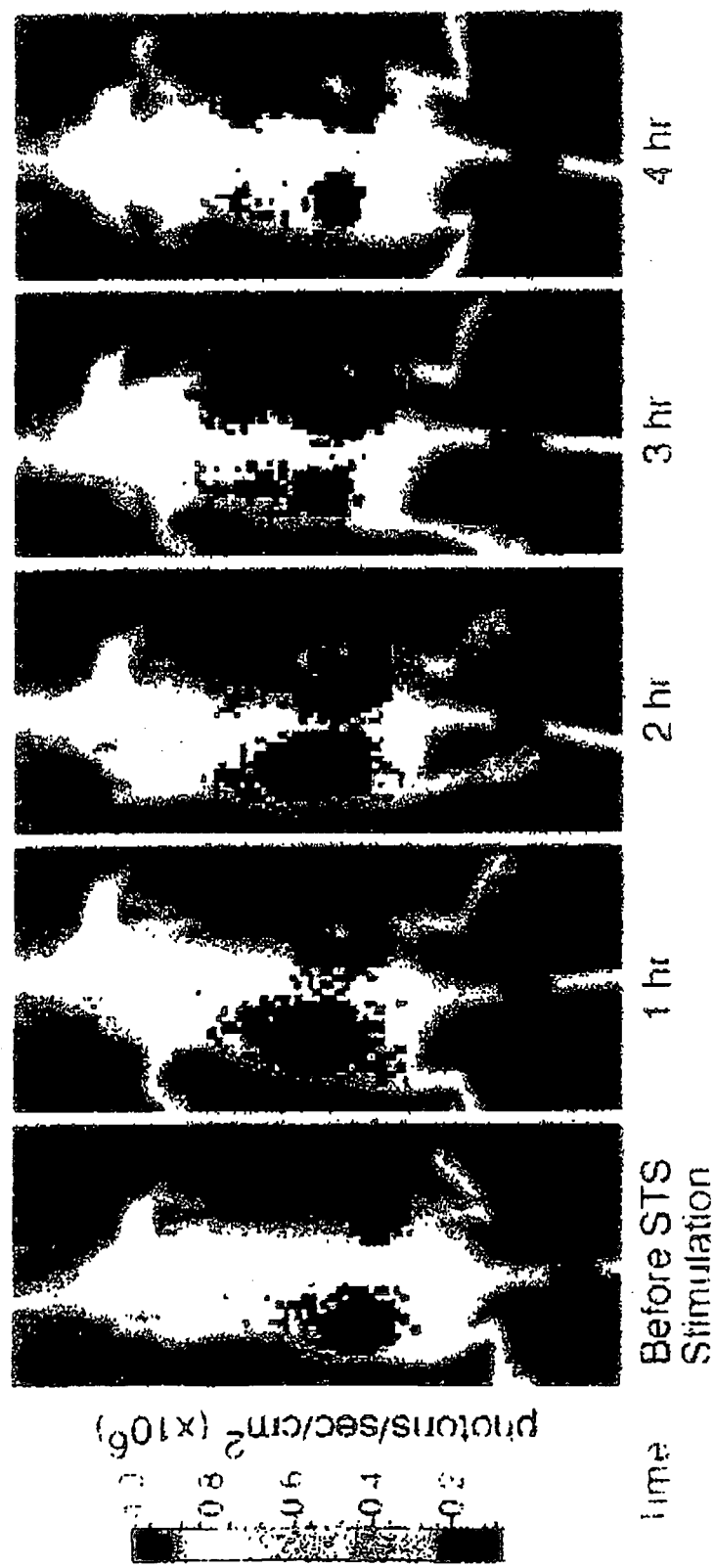
[FIG. 11] In vivo luminescence assay of mice carrying transiently transfected HeLa cells. The mice were subcutaneously implanted with HeLa cells expressing cyclic Fluc (right side) and full-length Fluc (left side). Images of the mice were taken at the indicated times after intraperitoneal injection of STS. A representative of three mice is shown.

In the Example, HeLa cells expressing cyclic Fluc were transplanted in the right side of the back of mice (FIG. 11). As the control experiment, HeLa cells expressing full-length Fluc were implanted on the left side. When the mice were injected intraperitoneally (i.p.) with STS (100 µg/kg of body weight), the observed images of the mice showed a significant increase in the luminescence signal intensity only from the right side, which was implanted with the cyclic Fluc. Three hours after the injection, the increase in the luminescence intensity was rapid; the luminescence gradually decreased thereafter. In the left side of the back of the mice, there is no significant change in the luminescence signal after the injection of STS. Thus, it indicates that the D-luciferin concentration in the bodies of mice were kept constant during the data acquisition.

Figure 12:
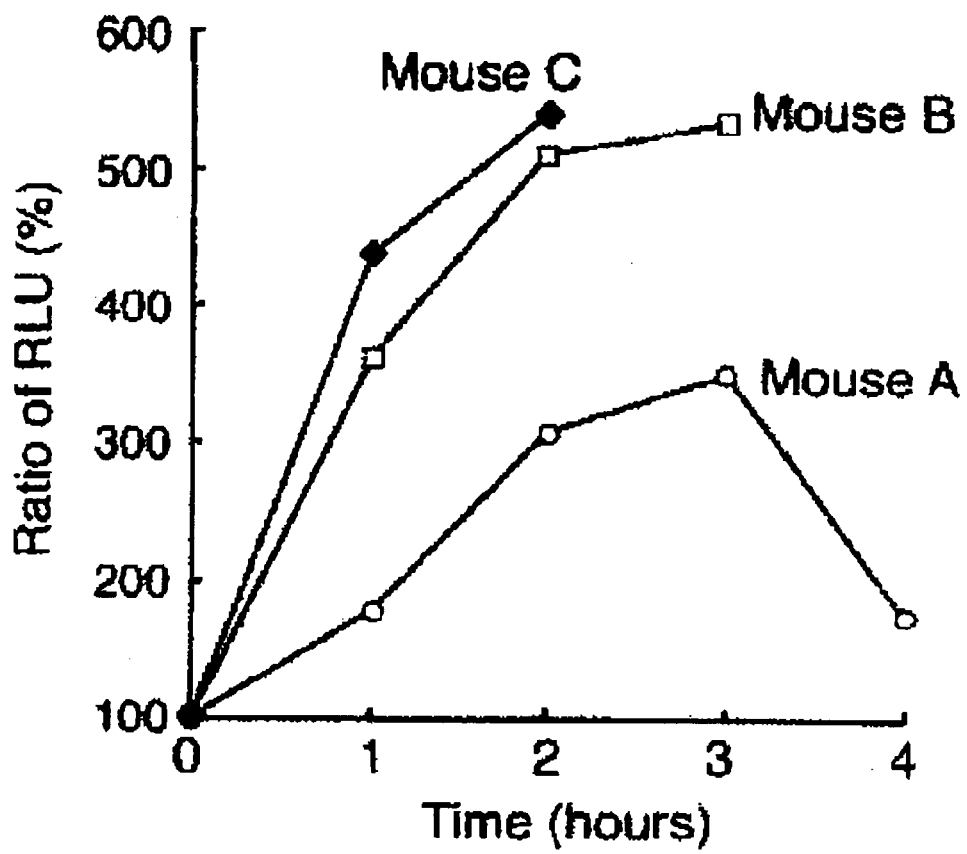
[FIG. 12] Time-dependent changes in the photon count from the implanted site in FIG. 11. The relative luminescence unit (RLU) is shown on the longitudinal axis, where RLU=LumR/LumL provided that luminescence intensity from the right side (LumR) is divided with the luminescence intensity from the left side (LumL), as shown in (A). A relative luminescence unit (RLU) was defined as follows: the luminescence intensity from the right side (LumR) was divided by that from the left side (LumL), as RLU (%)=LumR/LumL.

To quantitatively evaluate the effect of STS on caspase-3 activity, a relative luminescence unit (RLU) was defined as follows; the luminescence intensity from the right side (LumR) was divided by that from the left side (LumL), as RLU (%)=LumR/LumL. This calculation eliminates variations in the experimental conditions such as transfection efficiency, decomposition of the implanted cells, and the amount of injected D-luciferin circulating in the mice. FIG. 12 shows the temporal changes in the RLU, which was evaluated from the bioluminescence images at the indicated times two hours after the intraperitoneal STS injection, the RLU reached the maximum ratio of about 300 to 400% in comparison to the RLU before STS stimulation with STS. Hence, with in vivo sensing by cyclic Fluc reporter, the present system was capable for detection of the caspase-3 activity in real time upon stimulation with extraneous chemical compounds.

3. Discussion

In the Example, a method for the detection of caspase-3 activity in vitro and in vivo with a genetically encoded de novo reporter of cyclic Fluc generated by protein splicing, was demonstrated. The method of cell-based sensing with the reporter provided quantitative and real-time measurements of the extent of the caspase-3 activity in response to extracellular stimuli. The cyclic Fluc reporter further allowed noninvasive imaging of caspase-3 activity in living mice in a time-dependent manner.

The conventional methods for analyzing caspase-3 activity have mostly depended upon FRET-based indicators, using a pair of fluorescent organic chemical compounds or GFP derivatives (Reits, E. et al. (2003) Immunity 18, 97-108; Nagai, T. & Miyawaki, A. (2004) Biochem. Biophys. Res. Commun. 319, 72-7; Takemoto, K. et al. (2003) J. Cell Biol. 160, 235-43; Xu, X. et al. (1998) Nucleic Acids Res. 26, 2034-5; Mahajan, N. P. et al. (1999) Chem. Biol. 6, 401-9). By the FRET-based methods, spatial information over time about the caspase-3 activity in single viable cells can be obtained. However, the FRET-based methods have several limitations in screening and in vivo imaging of chemical compounds. Specifically, the reasons are as follows: the information obtained by the methods is semi-quantitative information; because the FRET probe show a very small spectral change, the sensitivity is limited. Among the apoptotic reagents or drug candidates, there are fluorescent or light-absorbing compounds, such as apoptosis-inducing Act D and wortmannin catabolites. These may disturb the observed fluorescence signals. The precision of the fluorescence observed by fluorescence microscopy is not very high, because the number of analyzed cells is quite limited. When applied to living mice, the low-wavelength excitation light for FRET is scattered by the organs such as hemoglobin, lipids and dyes, which hamper the detection of emitted fluorescence. By the present method using cyclic Fluc, these limitations can be overcome to detect the caspase-3 activity due to background-free luminescence signals generated during apoptosis. The activity of cyclic Fluc was found to be quite low and therefore enabled highly sensitive detection of the activity of caspase-3. Moreover, the number of cells analyzed in a single well was $10^4$ to $10^6$ cells, which was enough to precisely evaluate the extent of the activity of caspase-3 induced with extracellular stimuli. Using the indicator, therefore, the detection at a high precision and high accuracy with background-free luminescence can be done, which is advantageous for quantitatively evaluating the apoptosis extent in living cells and animals.

It is reported that intein-mediated cyclization of peptide backbones has been demonstrated for analysis of protein folding of dihydrofolate reductase (DHFR) and GFP (Scott, C. P. et al. (1999) Proc. Natl. Acad. Sci. USA. 96, 13638-43; Iwai, H. et al. (2001) J. Biol. Chem. 276, 16548-54). A method of short-peptide cyclization with randomly variable amino acids has been shown to yield a potential inhibitor of intracellular signaling. A method of short peptide cyclization with randomly variable amino acids has been shown to yield a potential inhibitor of intracellular signaling, as reported (Kinsella, T. M. et al. (2002) J. Biol. Chem. 277, 37512-8). Compared with the existing cyclization techniques, the most unique feature of the present cyclic Fluc is that there is a large difference in the luminescence signals between cyclic and linear form, regardless of similarity in molecular weights and amino acid sequences. Presently, the substrate peptide for caspase-3 was connected to N- and C-terminal end of Fluc, so that the enzyme activity was decreased, which was rapidly restored after digestion of the substrate by caspase-3. The PEST sequence on the C-terminus plays a role in degradation of the unspliced precursor protein. The presence of the PEST sequence is important for high-sensitivity detection, since such unspliced precursor protein generates high background luminescence. These unique features of the indicator using the cyclic luciferase are absolutely different from those of modified luciferase indicators reported previously. In the existing reports, specifically, protein interactions or nuclear protein transfer are analyzed using luciferase on the basis of the complementation or reconstruction of split luciferase (Paulmurugan, R. et al. (2002) Proc. Natl. Acad. Sci. USA. 99, 15608-13; Ozawa, T. et al, (2001) Anal. Chem. 73, 2516-21; Kim, S. B. et al. (2004) Proc. Natl. Acad. Sci. USA. 101, 11542-7; Luker, K. E. et al. (2004) Proc. Natl. Acad. Sci. USA. 101, 12288-93; Remy, I. & Michnick, S. W. (2006) Nat. Methods. 3, 977-9).

Another report tells about the detection of NF-κB signal transduction, using Fluc as a reporter, where Fluc is bound to the I κB and after ubiquitin modification, proteolysis is promoted (Gross, S. & Piwnica-Worms, D. (2005) Nat. Methods. 2, 607-14). Therefore, the method for preparing the cyclic Fluc by protein splicing is unique methodologically, so using the method, a luciferase indicator for detecting other proteases may additionally be designed.

Presently, it was shown quantitative effect of both apoptosis-inducting and -inhibiting chemical compounds on caspase-3 activity. Unexpectedly, the luminescence signal generated from the cells treated with 100 μM Z-VAD-FMK was reduced in 50% of the signals generated from vehicle-treated cells (FIG. 5). The results indicate that the mild ischemic conditions of cells upon transfection induced a basal activation of caspase-3 and that Z-VAD-FMK completely inhibited the basal caspase-3 activities. Additionally, cyclic Fluc provided information concerning the spatial and temporal patterns of caspase-3 activity in living mice. Thus, rapid assessment of potential therapeutic chemical compounds in a fully quantitative manner is possible.

In the Example, in conclusion, it was demonstrated the usefulness of cyclic Fluc for quantitative detection of caspase-3 activity in living cells and animals. Cell-based analysis by using the presented assay with cyclic Fluc allows for precise and quantitative measurement of caspase-3 activity because a statistically significant number of cells can be analyzed. The response of cyclic Fluc upon caspase-3 activation is very fast, which enables high throughput screening and characterization of therapeutic anticancer drugs and caspase inhibitors. Since the amount of proves, in general, are controllable with the conventional stable expression or viral infection techniques, the use of such transfection techniques may improve the specification of the present method. Herein, the in vivo real-time imaging of caspase-3 activity in living mice was shown. Chemical compounds, in many cases, are metabolized or chemically modified in living mice. Effective concentrations of the compounds can be estimated noninvasively by using the present method. Effective concentrations of such compounds can be estimated noninvasively by using the present method. Therefore, a genetically encoded reporter facilitates the development of transgenic animals that express the cyclic Fluc in a specific tissue under controllable promoters. Although the feasibility for only caspase-3 activity is described herein, modifications in the substrate region of the cyclic Fluc reporter will enable the monitoring of other protease activities. This basic concept is also applicable to luciferases emitting light of different wavelengths with D-luciferin.

In conclusion, the use of the present approach allows for high-speed sensing and real-time imaging covering a wide range of protease activities in living organisms.

Industrial Applicability

Because the indicator of the invention has a low molecular weight and enables the detection of activated protease in vitro or in viable cells, protease activation can be detected on real time in a noninvasive manner. Additionally, the signal intensity from the reconstructed luciferase is sufficiently high enough to be observed from the outside without any absorption into animal tissues, so that cells in an animal are used as subjects to detect the protease activation.

In particular, the indicator exerts its effects in screening for a factor influencing protease activation or inactivation in viable cells. In case that the subject is a drug candidate substance or the like, high-throughput screening is also possible.

The invention claimed is:

1. A recombinant indicator for an active protease, which is a circular form comprising a C-half fragment of a click beetle or firefly luciferase (Luc-C), an N-half fragment of firefly luciferase (Luc-N), and a substrate peptide for a protease,
   wherein the C-terminus of the Luc-N is linked with the N-terminus of the Luc-C, the N-terminus of the Luc-N is linked with the C-terminus of the substrate peptide, and the C-terminus of the Luc-C is linked with the N-terminus of the substrate peptide,
   wherein the N-half fragment of luciferase consists of amino acids residues 2 to 416 of SEQ ID NO: 5, and the C-half fragment of luciferase consists of of amino acids residues 399 to 550 of SEQ ID NO: 5;
   wherein the recombinant indicator is non-luminescent when in the circular form, and
   wherein the Luc-N and the Luc-C reconstructs an active luciferase upon digestion of the substrate peptide by the protease and is luminescent when digested into a non-circular form.

2. An expression vector encoding the recombinant indicator for an active protease of claim 1.

3. The expression vector of claim 2, wherein the recombinant indicator for an active protease is an indicator for monitoring protease activation in isolated cells.

4. A method for detecting protease activity in an in vitro assay system or an isolated cell, comprising:
   introducing the recombinant indicator for an active protease of claim 1 in the in vitro assay system or in the isolated cell, and
   measuring a signal of activated luciferase generated upon the degradation of the substrate peptide.

5. A method for screening a factor effecting protease activity in an in vitro assay system or in an isolated cell, comprising:
   introducing the recombinant indicator for an active protease of claim 1 in an in vitro assay system or an isolated cell containing inactive protease and/or active protease,
   contacting a candidate factor with the in vitro assay system or with the isolated cell,
   measuring the signal from the indicator of claim 1 before and after said contacting, and
   determining that the candidate factor is a protease-activating factor when the signal increases, and that the candidate factor is a protease-inactivating factor when the signal decreases.

6. A kit for detecting protease activity, comprising the recombinant indicator for an active protease of claim 1.

7. A kit for detecting protease activity, comprising the expression vector of claim 2.

* * * * *